(12) United States Patent
Dinarello et al.

(10) Patent No.: US 7,875,709 B2
(45) Date of Patent: Jan. 25, 2011

(54) NUCLEIC ACIDS ENCODING INTERLEUKIN-18 MUTANTS

(75) Inventors: Charles A Dinarello, Boulder, CO (US); Soo-Hyun Kim, Greenwood Village City, CO (US)

(73) Assignee: Ares Trading S.A. (CH)

( * ) Notice: Subject to any disclaimer, the term of this patent is extended or adjusted under 35 U.S.C. 154(b) by 0 days.

(21) Appl. No.: 12/404,458

(22) Filed: Mar. 16, 2009

(65) Prior Publication Data

US 2009/0286855 A1 Nov. 19, 2009

Related U.S. Application Data

(62) Division of application No. 10/094,153, filed on Mar. 8, 2002, now Pat. No. 7,524,488.

(60) Provisional application No. 60/274,327, filed on Mar. 8, 2001.

(51) Int. Cl.
*C07H 21/04* (2006.01)
*C12P 21/00* (2006.01)
*A61K 45/00* (2006.01)

(52) U.S. Cl. .................. 536/23.5; 435/69.52; 424/85.2

(58) Field of Classification Search .................... None
See application file for complete search history.

(56) References Cited

FOREIGN PATENT DOCUMENTS

WO 9959565 A1 11/1999

OTHER PUBLICATIONS

Pecceu F, et al. Human interleukin 1 beta fused to the human growth hormone signal peptide is N-glcosylated and secreted by Chinese hamstere ovary cells. Gene, 1991, vol. 97(2), p. 253-258.*
Dupre L et al. Immunostimulatory effect of IL-18-encoding plasmid DNA vaccination against murine Schistosoma mansoni infection. Vaccine, 2001, vol. 19(11-12), p. 1371-1380).*
Anderson, D.M., et al. (1997) "A. homologue of the TNF receptor and its ligand enhance T-cell growth and dendritic-cell function." Nature, 390, 175-179.
Bazan, J. F., et al. (1996) "A newly defined interleukin-1?" Nature 379, 591.
Born, T.L, et al. (2000) "A poxvirus protein that binds to and inactivates IL-18, and inhibits NK cell response." J Immunol 164,3246-54.
Childs, R., et al. (2000) "Regression of metastatic renal-cell carcinoma after nonmyeloablative allogeneic peripheral-blood stem-cell transplantation." N. Engl J Med 343, 750-8.
Cho, D., et al. (2000) "Interleukin-18 and the costimulatory molecule B7-1 have a synergistic anti-tumor effect on murine melanoma; implication of combined immunotherapy for poorly immunogenic malignancy." J Invest Dermatol,114, 928-34.
Coughlin, C.M., et al. (1998 ) "Interleukin-12 and interleukin-18 synergistically induce murine tumor regression which involves inhibition of angiogenesis." J Clin Invest Mar, 101,1441-52.

Engelmann, H., et al. (1989) "A tumor necrosis factor-binding protein purified to homogeneity from human urine protects cells from tumor necrosis factor toxicity." J. Biol. Chem. 264,11974-11980.
Engelmann, H., et al. (1990) "Two tumor necrosis factor-binding proteins purified from human urine. Evidence for immunological cross-reactivity with cell surface tumor necrosis factor receptors." J. Biol. Chem. 265,1531-1536.
Ghayur, T., et al. (1997) "Caspase-1 processes IFN-gamma-inducing factor and regulates LPS-induced IFN-gamma production." Nature 386, 619-623.
Gollob, J.A., et al. (2000) "Phase I trial of twice-weekly intravenous interleukin 12 in patients with metastatic renal cell cancer or malignant melanoma: ability to maintain IFN-gamma induction is associated with clinical response." Clin Cancer Res, 5, 1678-92.
Gong, J. H., et al. (1994) "Characterization of a human cell line (NK-92) with phenotypical and functional characteristics of activated natural killer cells." Leukemia 8:652.
Gu, Y., et al. (1997) "Activation of interferon-gamma inducing factor mediated by interleukin-1beta converting enzyme." Science 275, 206-209.
Kim, S.H., et al. (2000) "Structural requirements of six naturally occurring isoforms of the IL-18 binding protein to inhibit IL-18." Proc Natl Acad Sci U S A 97, 1190-5.
Kohno, K., et al. (1997) "IFN-gamma-inducing factor (IGIF) is a costimulatory factor on the activation of Th1 but not Th2 cells and exerts its effect independently of IL 12." J. Immunol. 158:1541-1550.
Kugler, A., et al. (2000) "Regression of human metastatic renal cell-carcinoma after vaccination with tumor cell-dendritic cell hybrids." Nat Med, 3, 332-6.
Nakamura, K., et al. (1989) "Endotoxin-induced serum factor that stimulates gamma interferon production." InfectImmun 57,590-5 issn: 0019-9567.
Nakamura, K., et al. (1993) "Purification of a factor which provides a costimulatory signal for gamma interferon production." Infect. Immun. 61, 64-70.
Novick, D., et al. (1989) "Soluble cytokine receptors are present in normal human urine." J. Exp. Med. 170,1409-14.
Novick, D., et al. (1992) "Soluble Interferon-alpha Receptor Molecules Are Present in Body Fluids." FEBS Lett 314, 445-8.
Novick, D., et al. (1994) "The Human Interferon alpha/beta Receptor—Characterization and Molecular Cloning." Cell 77, 391-400.
Novick, D., et al. (1999) Interleukin-18 Binding Protein: A Novel Modulator of the Th1 Cytokine Response. Immunity 10, 127, 36.
Okamura, H., et al. (1995) "Cloning of a new cytokine that induces IFN-gamma production by T cells." Nature 378, 88-91.
Puren, A.J., et al. (1999) "Gene expression, synthesis, and secretion of interleukin 18 and interleukin 1beta are differentially regulated in human blood mononuclear cells and mouse spleen cells." Proc Natl Acad Sci USA, 96, 2256-61.
Seki, S., et al. (2000) "The liver as a crucial organ in the first line of host defense: the roles of Kupffer cells, natural killer (NK) cells and NK1.1 Ag+ T cells in T helper 1 immune responses." Immunol Rev 174, 35-46.

(Continued)

*Primary Examiner*—Robert Landsman
*Assistant Examiner*—Bruce D Hissong
(74) *Attorney, Agent, or Firm*—Nixon Peabody LLP

(57) ABSTRACT

The invention provides mutants of IL-18 with lower affinity to IL-18BP than the wild type IL-18 molecule.

18 Claims, 6 Drawing Sheets

OTHER PUBLICATIONS

Simonet, W.S., et al. (1997) "Osteoprotegerin: a novel secreted protein involved in the regulation of bone density". Cell, 89, 309-19.

Slavin, S. (2000) "Immunotherapy of cancer with alloreactive lymphocytes." N Engl J Med 343, 802-3.

Slavin, S., et al. (2000) "Immunotherapy of hematologic malignancies and metastatic solid tumors in experimental animals and man." Bone Marrow Transplant Suppl 2:S54-7.

Tsutsui, H., et al. (1996) "IFN-gamma-inducing factor up-regulates Fas ligand-mediated cytotoxic activity of murine natural killer cell clones." J. Immunol. 157, 3967-73 issn: 0022-1767.

Tuting, T., et al. (1998) "Autologous human monocyte-derived dendritic cells genetically modified to express melanoma antigens elicit primary cytotoxic T cell responses in vitro: enhancement by cotransfection of genes encoding the Th1-biasing cytokines IL-12 and IFN-alpha." J Immunol. 160, 1139-47.

Urushihara, N., et al. (2000) "Elevation of serum interleukin-18 levels and activation of Kupffer cells in biliary atresia." J Pediatr Surg 35, 446-9.

Ushio, S., et al. (1996) "Cloning of the cDNA for human IFN-gamma-inducing factor, expression in *Escherichia coli*, and studies on the biologic activities of the protein." J. Immunol. 156, 4274-9.

Vigers, G.P., et al. (1997) "Crystal structure of the type-I interleukin-1 receptor complexed with interleukin-1beta." Nature 386,190-4.

Xiang, Y. and Moss, B. (1999) "IL-18 binding and inhibition of interferon gamma induction by human poxvirus-encoded proteins." Proc Natl Acad Sci U S A 96,11537-42.

Yasuda, H., et al. (1998) "Identity of osteoclastogenesis inhibitory factor (OCIF) and osteoprotegerin (OPG): a mechanism by which OPG/OCIF inhibits osteoclastogensis in vitro." Endocrinology, 139, 1329-37.

Hesselgesser et al. (1997), Alanine scan mutagenesis of chemokines, Methods Enzymol 287:59-69.

Evans et al. (1995), Mapping Receptor Binding Sites in Interleukin {IL}-1 Receptor Antagonist and IL-1 Beta by Site-directed Mutagenesis, J Biol Chem 270(19):11477-11483.

Kim et al. (1999), Roles of IFN Consensus Sequence Binding Protein and PU.1 in Regulating IL-18 Gene Expression, J Immun 163:2000-2007.

Fu et al. (2001) "Asp(126), Asp(130) and Asp(134) are Necessary for Human IL-18 to Elicit IFN-gamma Production from PBMC" Acta Biochimica et Biophysica Sinica 33(4):368-372.

Stryer, L. Biochemistry, 3rd ed., 1988, p. 18-20.

\* cited by examiner

Tyr Phe Gly Lys Leu Glu Ser Lys Leu Ser Val Ile Arg Asn Leu Asn
1                   5                        10                      15
Asp Gln Val Leu Phe Ile Asp Gln Gly Asn Arg Pro Leu Phe Glu Asp
            20                       25                      30
Met Thr Asp Ser Asp Cys Arg Asp Asn Ala Pro Arg Thr Ile Phe Ile
        35                      40                      45
Ile Ser Met Tyr Lys Asp Ser Gln Pro Arg Gly Met Ala Val Thr Ile
50                      55                      60
Ser Val Lys Cys Glu Lys Ile Ser Thr Leu Ser Cys Glu Asn Lys Ile
65                      70                      75                      80
Ile Ser Phe Lys Glu Met Asn Pro Pro Asp Asn Ile Lys Asp Thr Lys
            85                      90                      95
Ser Asp Ile Ile Phe Phe Gln Arg Ser Val Pro Gly His Asp Asn Lys
                100                     105                     110
Met Gln Phe Glu Ser Ser Ser Tyr Glu Gly Tyr Phe Leu Ala Cys Glu
            115                     120                     125
Lys Glu Arg Asp Leu Phe Lys Leu Ile Leu Lys Lys Glu Asp Glu Leu
        130                     135                     140
Gly Asp Arg Ser Ile Met Phe Thr Val Gln Asn Glu Asp.
145                     150                     155

SEQ ID NO: 2

*FIG. 1B*

NUCLEIC ACIDS ENCODING INTERLEUKIN-18 MUTANTS

CROSS-REFERENCE TO RELATED APPLICATIONS

The present application is a Divisional of U.S. Utility application Ser. No. 10/094,153 filed Mar. 8, 2002, which issued on Apr. 28, 2009 as U.S. Pat. No. 7,524,488, and which claims benefit under 35 U.S.C. §119(e) of the U.S. provisional application Ser. No. 60/274,327, filed Mar. 8, 2001, the contents of which are incorporated herein by reference in their entirety.

FIELD OF THE INVENTION

The present invention relates to IL-18 mutants having enhanced biological activity with respect to the wild type protein.

BACKGROUND OF THE INVENTION

In 1989, an endotoxin-induced serum activity that induced interferon-γ (IFN-γ) obtained from mouse spleen cells was described (Nakamura et al., 1989). This serum activity functioned not as a direct inducer of IFN-γ but rather as a co-stimulant together with IL-2, IFN-α/β, TNF or mitogens. An attempt to purify the activity from post-endotoxin mouse serum revealed an apparently homogeneous 50-55 kDa protein (Nakamura et al., 1993). Since other cytokines can act as co-stimulants for IFN-γ production, the failure of neutralizing antibodies to IL-1, IL-4, IL-5, IL-6, or TNF to neutralize the serum activity suggested it was a distinct factor. In 1995, the same scientists demonstrated that the endotoxin-induced co-stimulant for IFN-γ production was present in extracts of livers from mice preconditioned with *P. acnes* (Okamura at al. 1995). In this model, the hepatic macrophage population (Kupffer cells) expand and in these mice, a low dose of bacterial lipopolysaccharide (LPS), which in non-preconditioned mice is not lethal, becomes lethal. The factor, named IFN-γ-inducing factor (IGIF) and later designated interleukin-18 (IL-18), was purified to homogeneity from 1,200 grams of *P. acnes*-treated mouse livers. Degenerate oligonucleotides derived from amino acid sequences of purified IL-18 were used to clone a murine IL-18 cDNA (Okamura et al., 1995). Messenger RNAs for IL-18 and interleukin-12 (IL-12) are readily detected in activated macrophages. IL-18 does not induce IFN-γ by itself, but functions primarily as a co-stimulant with mitogens or IL-12. The human cDNA sequence for IL-18 was reported in 1996 (FIG. 1A SEQ ID NO:1).

Interleukin IL-18 shares structural features with the IL-1 family of proteins (Nakamura et al., 1993; Okamura et al., 1995; Ushio et al., 1996; and Bazan et al., 1996). Unlike most other cytokines, which exhibit a four-helix bundle structure, IL-18 and IL-1β have an all β-pleated sheet structure (Tsutsui et al., 1996). Similarly to IL-1β, IL-18 is synthesized as a biologically inactive precursor (proIL-18), lacking a signal peptide (Ushio et al., 1996). The IL-1β and IL-18 precursors are cleaved by caspase 1 (IL-1β-converting enzyme, or ICE), which cleaves the precursors after an aspartic acid residue in the P1 position. The resulting mature cytokines are readily released from the cell (Ghayur et al., 1997; and Gu et al., 1997).

IL-18 is a co-stimulant for cytokine production (IFN-γ, IL-2 and granulocyte-macrophage colony stimulating factor) by T helper type I (Th1) cells (Kohno et al., 1997) and also a co-stimulant for FAS ligand-mediated cytotoxicity of murine natural killer cell clones (Tsutsui et al., 1996).

Th1 lymphocytes are involved in the immune responses against tumors (Seki et al., 2000). Th1 responses include the secretion of the cytokines IL-2, IL-12, IL-18 and IFN-γ, as well as the generation of specific cytotoxic T lymphocytes recognizing specific tumor antigens. The Th1 response is also a vital arm of host defense against many microorganisms. However, the Th1 response can also be associated with non-desirable effects such as the development of several autoimmune diseases, inflammation and organ transplant rejection.

Attempts to express the mature form of IL-18 in *E. coli* using a vector encoding the mature protein did not provide a fully active cytokine. An efficient expression system for the generation of the fully biologically active human IL-18 has been developed for therapeutic uses, e.g. in malignancies, or any condition where interferon-γ induction is desired (WO 00/61768). In this system, the IL-18 precursor caspase-1 cleavage site has been changed to a factor Xa site (ICE/Xa), and a vector encoding IL-18 ICE/Xa precursor was used for transformation of *E. coli*. Following expression of this IL-18 precursor in *E. coli* the mature IL-18 was generated by factor Xa cleavage in vitro. This mature IL-18 generated by factor Xa cleavage was fully active.

Cytokine binding proteins (soluble cytokine receptors) are usually the extracellular ligand binding domains of their respective cell surface cytokine receptors. They are produced either by alternative splicing or by proteolytic cleavage of the cell surface receptor. These soluble receptors have been described in the past: for example, the soluble receptors of IL-6 and IFN-γ (Novick et al., 1989), TNF (Engelmann et al., 1989; and Engelmann et al., 1990), IL-1 and IL-4 (Maliszewski et al., 1990), IFN-α/β (Novick et al., 1994; Novick et al., 1992). One cytokine-binding protein, named osteoprotegerin (OPG, also known as osteoclast inhibitory factor—OCIF), a member of the TNFR/Fas family, appears to be the first example of a soluble receptor that exists only as a secreted protein (Anderson et al., 1997; Simonet et al., 1997; Yasuda et al., 1998).

An interleukin-18 binding protein (IL-18BP) was affinity purified, on an IL-18 column, from urine (Novick et al., 1999). IL-18BP abolishes IL-18 induction of IFN-γ and of IL-8, activation of NF-kB in vitro and induction of IFN-γ in vivo. IL-18BP is a soluble circulating protein which is constitutively expressed in the spleen, and belongs to the immunoglobulin superfamily. The most abundant IL-18BP isoform, the spliced variant isoform a, exhibits a high affinity for IL-18 with a rapid on-rate and a slow off-rate, and a dissociation constant (Kd) of approximately 400 pM (Kim et al., 1999).

The residues involved in the interaction of IL-18 with IL-18BP have been described through the use of computer modeling (Kim et al., 1999) and based on the interaction of IL-1β with the IL1R type I (Vigers et al., 1997). In the model for IL-18 binding to the IL-18BP, the Glu residue at position 42 the and Lys residue at position 89 of IL-18 have been proposed to bind to Lys-130 and Glu-114 in IL-18BP, respectively (Kim et al., 1999).

IL-18 is constitutively present in many cells (Puren et al., 1999) and circulates in healthy humans (Urushihara et al., 2000). The high affinity of IL-1BP to IL-18 as well as the high concentration of IL-18BP found in the circulation (20 fold molar excess over IL-18), represents a unique situation in cytokine biology. Therefore, most, if not all, of the IL-18 molecules in the circulation is bound to the IL-18BP. The circulating IL-18BP which competes with cell surface receptors for IL-18, may act as a natural anti-inflammatory and an immunosuppressive molecule.

Viral agents encode IL-18BP like proteins, for example, *M. contagiosum* viral proteins MC53 and MC54 share a significant homology to mammalian IL-18BP (Novick et al., 1999). *M. contagiosum* proteins MC53 and MC54 possess the ability to bind and neutralize human IL-18 in a fashion similar to that of IL-18B (Xiang and Moss, 1999). The ectromelia poxvirus p13 protein, which is homologous to IL-18BP, binds human IL-18 and inhibits its activity in vitro. Mice infected with a p13 deletion mutant virus exhibited decreased levels of infectivity (Born et al., 2000). Therefore infectivity degree seems to correlate with the presence of IL-18BP.

The high levels of circulating IL18BP may represent a natural defense against a runaway Th1 response to infection and development of autoimmune diseases. However, IL-18 contributes to the Th1 response which is important in host defense against tumors. Therefore, IL-18BP may bring about failure of the host to develop cytotoxic T cells directed against tumor cells. Indeed, there is evidence that IL-18 promotes host defense against tumors in mice. For example, in syngeneic mice, murine mammary carcinoma cells expressing murine IL-12 or murine IL-18 were less tumorogenic and formed tumors more slowly than did control non-expressing cells (Coughlin et al., 1998). Antibody neutralization studies revealed that the antitumor effects required IFN-γ. In another study, systemically administration of IL-18 to experimental animals in combination with B16 melanoma expressing B7-1 (CD80) resulted in dramatic suppression of melanoma formation, tumor growth, and a significant improvement in survival (Cho et al., 2000).

Cytokines are used as adjuvant to increase the effectivity of immunotherapy in cancer. For example, IL-2 is administered for renal cell carcinoma or melanoma (Gollob et al., 2000). Often, one important consequence of the treatment with cytokines is severe systemic toxicity profiles. Using cytokines, expressed by the patient's own tumor or dendritic cells, is a logical solution to the problem. Yet, if IL-18 will to be used locally, as adjuvant in tumor immunotherapy, the ability of the constitutive levels of IL-18BP to neutralize IL-18 in the local environment would still be exerted and consequently its effectivity is greatly diminished.

The use of non-myeloablative allogeneic transplants, so-called mini transplants, to treat leukemia and solid tumors is increasingly successful in inducing graft-versus-leukaemia and graft-versus-tumor reactions (Slavin S, 2000; Slavin et al., 2000). Two studies that used either allogeneic peripheral blood stem cells (Childs et al., 2000) or dendritic cells (Kugler et al., 2000) to treat patients with metastatic renal cell carcinoma met a remarkable success. Although these studies need to be extended and confirmed, the concept that an ongoing graft-versus-tumor reaction is exploitable for immunotherapy in cancer is gaining acceptance (Slavin, 2000). Since IL-18 appears to be involved in these successful therapeutic approaches, a further improvement may be achieved if the neutralizing effect of IL-18BP can be abolished.

Mutants of IL-18 (IFN-γ, inducing factor) are described in EP0845530. The described IL-18 mutants are molecules in which 1, 2, 3 or all 4 cysteine residues in IL-18 (FIG. 1B) were replaced by serine or alanine residues. These mutants contained an intact consensus sequence (FIG. 1B). All the isolated mutants exhibit higher stability than wild type IL-18. The degree of stability of the mutants is directly proportional to the number of Cys residues replaced in the molecule. EP0845530 is silent on the ability of IL-18BP to neutralize these mutants.

The generation and therapeutic use of fully active IL-18 mutants unable to bind or bind with low affinity to IL-18BP, is therefore highly advantageous.

SUMMARY OF THE INVENTION

The present invention relates to an IL-18 mutant polypeptide, comprising mutations in one or more amino acid residues which are involved in its interaction with IL-18 binding protein. More specifically, the mutations are substitutions, preferably non-conservative, additions or deletions. The residues mutated in said polypeptide may be selected from Glu-42, Ile-85, Met-87, Lys-89, Met-96, Asp-130, Lys-132, Pro-143, Met-149, and Leu-189, preferably, Glu-42 and Lys-89.

In one embodiment, the Glu-42 or Lys-89 or both Glu-42 and Lys-89 are replaced with a non-polar amino acid, preferably alanine.

In addition, the invention provides for a DNA encoding said polypeptide, preferably encoding a polypeptide of SEQ ID NO:3, SEQ ID NO:4, SEQ ID NO:5, SEQ ID NO:6, SEQ ID NO:7 or SEQ ID NO:8.

In one embodiment, DNA encoding SEQ ID NO:6, SEQ ID NO:7, SEQ ID NO:8 is fused to a signal peptide, preferably that of the hGH. Moreover, the invention also provides a vector comprising said DNA capable of expressing the polypeptide encoded by said DNA in an appropriated host cell, e.g. a prokaryotic or eukaryotic host cell.

In addition, the present invention provides for pharmaceutical compositions comprising said a polypeptide for the treatment of diseases which are prevented or alleviated by Th1 responses, preferably for treatment of viral disease or cancer.

BRIEF DESCRIPTION OF THE FIGURES

FIG. 1B shows the amino acid sequence of the mature IL-18. The consensus sequence among different species of IL-18 are enclosed in the white boxes. The cystidines are underlined. The dark boxes show the residues mutated in IL-18 according to this invention.

The pro IL-18 (ICE/Xa) cDNA was ligated into the BLUE-SCRIPT plasmid (Stratagene) by EcoRI and BamHI (GIBCO/BRL) restriction sites. This plasmid served for sequence confirmation. The predicted amino acid sequence encoded is shown in SEQ ID NO:2. For E. coli expression, the IL-18 DNA insert was re-ligated into the pPROEX HTa vector (GIBC0/BRL) with the use of EcoRI and XbaI sites (originating in BLUESCRIPT). In this vector, the resulting protein is N-terminal fused to a histidine tag.

Example 2

Construction of the E42A, K89A and E42A/K89A Mutants

Figure 2:
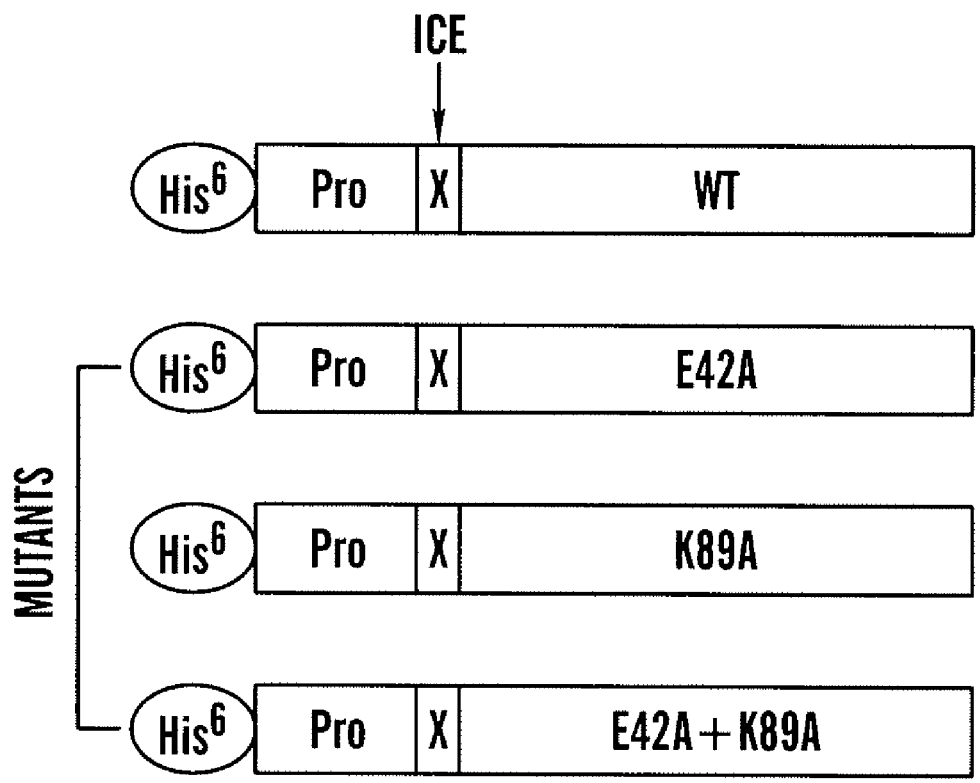
FIG. 2 shows the schematic representation of the IL-18 mutants according to the invention. The His-6 indicates the location of the six histidines fused in the N terminus of the IL-18 precursor propiece. The arrow indicates the ICE cleavage site as replaced by the factor Xa cleavage site (x). WT indicates the wild-type mature IL-18. E42A indicates Glu-42 to Ala mutation, K89A indicates Lys-89 to Ala mutation and E42A/K89A indicates double mutation. On the basis of precursor /x/WT, three IL-18 mutants (E42A, K89A and E42A+K89A) were generated by two step PCR.

Mutations in IL-18 were created in residues predicted to be important for the binding to the inhibitor IL-18BP (Kim et al., 2000). Three mutants: E42A, K89A, and F 42A/K89A, were generated. The mutations were achieved by two PCR reactions, as described in example 1, using the primers and templates described below (the primers are shown in FIG. 2).

E42A Mutant

PCR reaction 1—The pair of primes used for preparing the mutant E42A were: pair A—Pr 1 (example 1) and the reverse primer (Pr 5) 5'-TAA TTT AGA TGC AAG CTT GCC (SEQ ID NO:15) encoding alanine instead of glutamic acid (E 42), and Pair B the sense primer (Pr 6) 5' GGC AAG CTT GCA TCT AAA TTA (SEQ ID NO:16) encoding Alanine in exchange for Glutamic acid (GAA to GCA) and the reverse primer Pr 4 (example 1), using pro IL-18 (ICE/Xa) as a template in the PCR reaction.

PCR reaction 2: The two DNA fragments obtained in PCR reactions 1 were used as templates for the second PCR reaction using primers Pr1 and Pr 4.

K89A Mutant

PCR reaction 1: The pair of primes used for preparing the mutant K89A were pair A Pr 1 (example 1) and the reverse primer (Pr 7) 5' CTG GCT ATC TGC ATA CAT ACT (SEQ ID NO: 17) encoding alanine instead of lysine (K 89), and pair B the sense primer (Pr 8) 5' AGT ATG TAT GCA GAT AGC CAG (SEQ ID NO:18) encoding alanine instead of Lysine (AAA to GCA) with the reverse primer Pr 4 (Example 1) using pro IL-18 (ICE/Xa) as the template for the first PCR reaction.

PCR reaction 2: The two DNA fragments obtained in the PCR reaction 1 were used as templates for the second PCR reaction using primers Pr1 and Pr 4.

E42A/K89A Mutant

For the double mutation E42A/K89A, the primer used were the same as for the preparation of the F-42A mutation and mutant K89A cDNA was used as the template in the reaction.

Figure 1A:
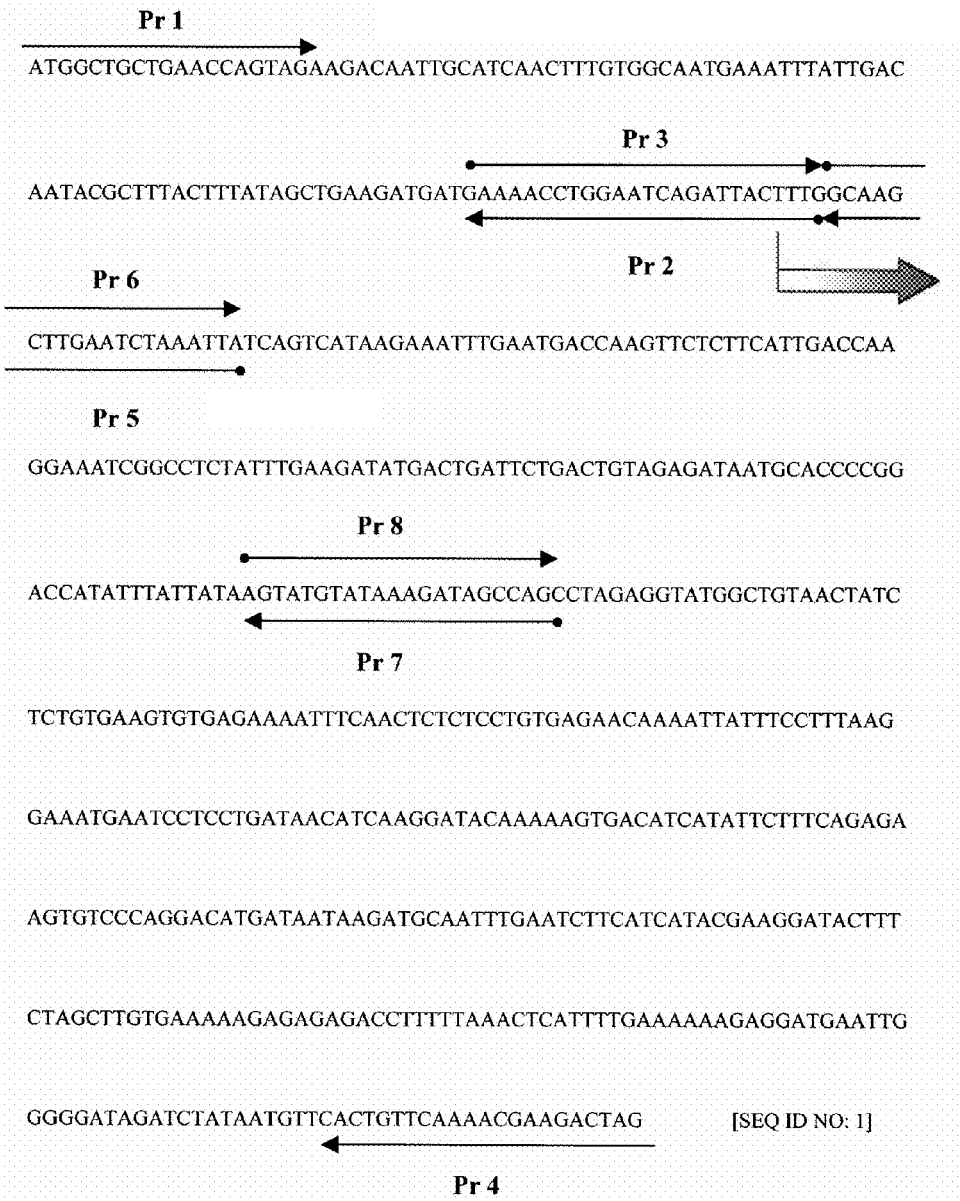
FIG. 1A shows the nucleotide sequence encoding the WT IL-18 precursor and the location of primers used to construct the different mutated IL-18 proteins. The broad arrow indicates where the mature IL-18 protein coding sequence begins.

Each of the three IL 18 mutated genes were ligated into the BLUESCRIPT vector for sequence confirmation. The predicted amino acid sequence for the precursor IL-18 E42A, K89A and E42A/K89A mutants are shown in SEQ ID NO:3, SEQ ID NO:4 SEQ ID NO:5, respectively. For E. coli expression, each of three IL-18 DNA inserts were re-ligated into the pPROEX HTa vector (GIBC0/BRL) with the use of EcoRI and XbaI sites. The resulting protein is N-terminal fused to histidine (FIG. 1).

Example 3

Protein Expression and Purification

The IL18 mutant precursors were expressed in E. coli, affinity purified by virtue of the histidine tag and the respective mature molecules were generated by proteolytic cleavage with factor Xa.

Each of the four pPROEX HTu/IL-18 plasmids (WT and three mutants) was introduced into competent E. coli cells of the DHQ strain (GIBCO/BRL) and expressed as described (11). An overnight culture of 25 ml served as the inoculum for a 450 ml of LB culture containing 100 µg/ml ampicillin and grown until it reached a cell density of 0.6 1 OD600. Protein expression was induced by treatment with isopropylthiogalactoside (IPTG 0.3 mM), and incubation continued at 37° C. with shaking for 3 h. The cultured bacteria cells were harvested by centrifugation (5,000×g for 15 min at 4° C.), and the pellet was suspended in 30 ml of TALON® buffer (50 mM $NaH_2PO_4$/20 mM Tris HCl/100 mM NaCl, pH 8). Cells were lysed by sonication (2×30 s bursts) on ice. The soluble protein was obtained by centrifugation (4,000×g for 30 min at 4° C.) and applied to a 3 ml mini-TALON® column (CLONTECH). The TALON® column was then washed with 30 bed volumes of TALON® buffer and eluted with 6 ml of 100 mM imidazole in TALON® buffer. The eluant was dialyzed against factor Xa buffer (20 mM Tris HCl/150 mM NaCl/2 mM $CsCl_2$) at 4° C. for 20 h. The 0.2 ml of TALON® affinity-purified N-terminus His×6 fusion proIL-18 was incubated with 4 µg of factor Xa enzyme (New England Biolabs) for 4 h at room temperature in the presence of 2 mM phenylmethylsulfonyl fluoride (GIBCO/BRL). The amount of IL-18 produced was monitored by a specific ELISA (R&D Systems). The amino acid sequence predicted for the mature IL-18 WT, E42A, K89A and E42A/K89A mutants are shown in sequences SEQ ID NO:6, SEQ ID NO:7 SEQ ID NO:8, respectively.

Example 4

Characterization of the E42A, K89A and E42A/K89A IL-18 Mutant Proteins by Western Blot The purified IL-18 mutants were subjected to western blot analysis with a polyclonal antibody and a monoclonal antibody specific for the mature IL-18.

Equal amounts of TALON® affinity purified precursor and mature protein (after cleavage by factor Xa) the WT and mutant IL-18 forms, were resolved by SDS/PAGE (10% acrylamide) under reducing conditions. The proteins were transferred to nitrocellulose membranes and then incubated with the primary antibodies (rabbit anti-human IL-18 polyclonal antibody or monoclonal antibody clone 8-31-4 (IgG2a) which were raised against the recombinant mature form of human IL 18 (Puren et al., 1999) which also recognize precursor IL-18). After 24 h incubation, the corresponding second antibody, goat anti-mouse or donkey anti-rabbit IgG peroxidase (Jackson Immuno Research), was added and developed by ECL (New England Nuclear Life Science Products).

The staining of proIL-18 by polyclonal rabbit anti-human IL-18 was of equal intensity for the WT and each of the three mutants. Similarly the signals obtained with the mature forms of WT and IL-18 and each of the three mutants using the polyclonal antiserum were of equal intensity. The apparent molecular weigh indicated that the different IL-18 forms were of the correct size. In contrast, when the monoclonal antibody is used, the two mutants K89A and E42A/K89A, appear to stain more intensely than the WT and the E42A mutant, suggesting that the affinity of the monoclonal antibody is greater for these mutants. These results suggest that mutants K89A and E42A/K89A may have a different conformation resulting in higher affinity.

Example 5

Characterization of the Biological Activity of E42A, K89A and E42A/K89A IL-18 Mutant Proteins The purified mature forms of IL-18/ICE/Xa were analysed for the co-induction of IFN-γ in human natural killer cells (NKO described in example 8), in PBMCs (described in example 7) and for the induction of IL-8 in PBMCs.

IL-18 does not induce IFN-γ in these cells unless IL-12 (or IL-15) is used as a co-stimulator. Low concentrations of IL-12 (1-2 ng/ml 12 (PreproTech Rocky Hill, N.J.)) induce a small amount, of IFN-γ, however, treatment with IL-12 together with IL-18 greatly augments IFN-γ production. IFN-γ produced was monitored in the cell as described in example 9. The induction of IFN-γ in NKO cells by WT IL-18/ICE/Xa and IL-12 was found to be comparable to that induced by recombinant mature human IL-18 resulting from ICE processing of proIL-18 (Gu et al., 1997) and IL-12. These results indicate that the IL-18 was correctly assembled in *E. coli* and correctly processed by factor Xa.

Figure 3A:
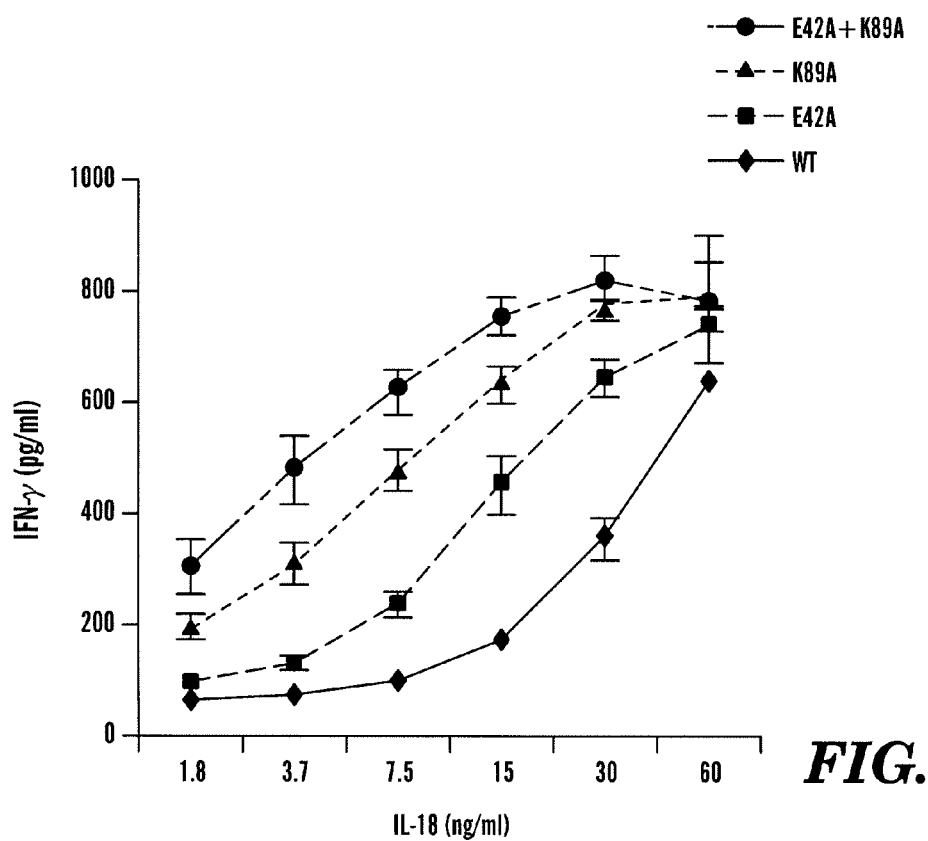
FIG. 3A shows the induction of IFN-γ in NKO cells by IL-18 WT and mutant protein at concentrations shown under the x axis in FIG. 3B and in the presence of IL-12 (0.5 ng/ml)

To test the activity of the mutated IL-18, the induction of IFN-γ production by stimulation with the mutant or WT IL-18 together with IL-12 was assessed in NKO cells (statistical analyses are described in example 10). As shown in FIG. 3A, WT IL-18 was active as an inducer of IFN-γ, beginning at 7.5 ng/ml and increasing progressively up to 60 ng/ml (the highest concentration tested). Each of the three mutated IL-18 forms exhibited biological activity greater than that of WT in these cells. For example, the single mutation E42A was twice as active as the WT form at each of the concentrations tested. The single mutation KB9A was four times more active than the WT at a concentration of 7.5 ng/ml. The double mutation E2A/K89A resulted in the most active IL-18. As shown in FIG. 3A, the E42A_mutated IL-18 induced 600 pg/ml IFNγ, the maximal activity observed by pretreatment with 60 ng/ml IL-18 WT, at a concentration of 30 ng/ml, the K89A mutant at a concentration of 15 ng/ml and the double mutant at a concentration of 7.5 ng/ml. The mutants E42A, K89A and double mutant were therefore 2, 4 and 8 folds more potent than the WT, respectively.

Figure 3B:
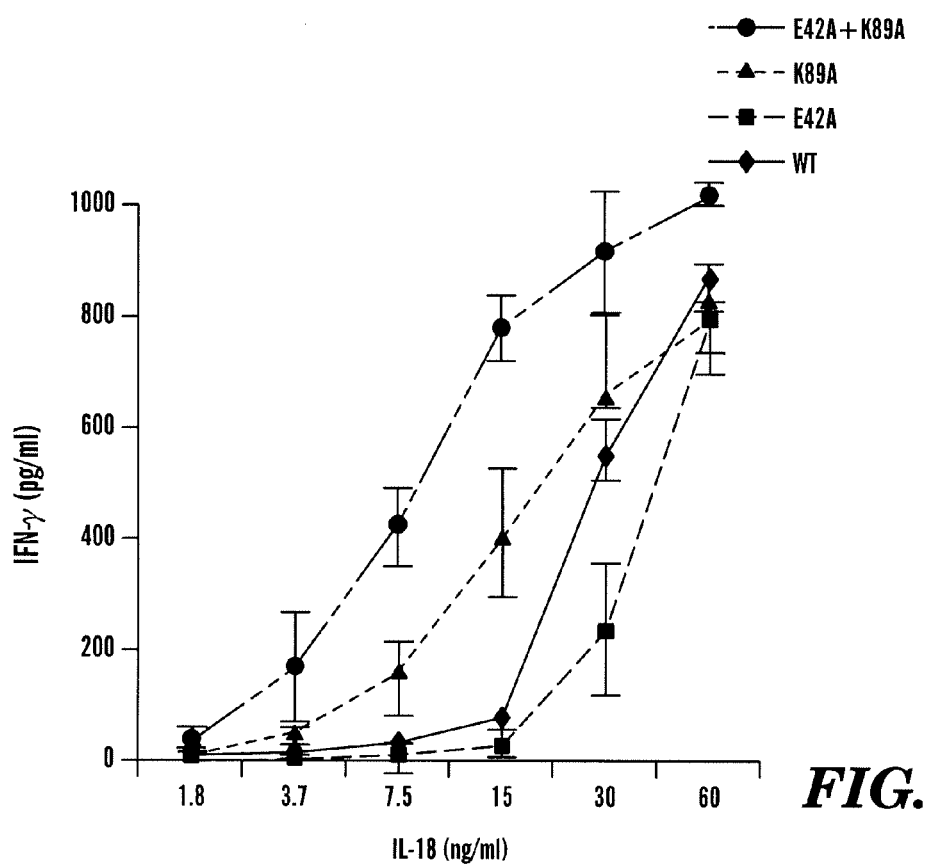
FIG. 3B shows the induction of IFN-γ in PBMCs cells by IL-18 WT and mutant protein at concentrations shown under the x axis and in the presence of IL-12 (1.0 ng/ml).

Similar results were observed when IFN-γ production was tested in freshly isolated human PBMCs (example 7). In these cells, the co-stimulation of IL-12 and IL-18 resulted, in IFN-γ, production, whereas neither of the two cytokines alone could induce IFNγ. The double mutant E42A/K89A was the most active (FIG. 3B).

The results indicate that replacement of the two charged amino acids Glu 42 and/or Lys 89 by Ala residues consistently bring about an increase in the biological activity of IL-18.

IL-18 is known to induce IL-8 in CD 14+ cells in PBMC preparations (described in example 7). Although IL-18 induces IL-8 production in these cells without the need of IL-12 co-stimulation, the induction of IL-8 requires higher concentrations of IL-18 than induction of IFN-γ. Induction of IL-8 by IL-18 WT and mutant stimulation of PBMCs was therefore tested. The IL-8 produced was monitored in the cell media by the specific assay described in example 9. FIG. 4 shows that although the two single mutations were comparable to the WT in the induction of IL-8, the double mutated IL-18 induced significantly more IL-8 (3.5 fold) than the wild type version.

These results indicate that the double mutant, E42A/K89A exhibits the highest biological activity.

Example 6

Neutralization of IL-18 Mutants by IL-18BP

The mutations were designed in residues predicted to be important for IL-18 binding by the inhibitor IL-18BP. The ability of IL-18BP to neutralize the biological activity of IL-18, e.g. IFN-γ production (example 8), was therefore specifically assessed.

Different concentrations of IL-18BP ("a" isoform of CHO cell produced recombinant his-6-tagged human IL-18BP (supplied by Interpharm Laboratories, Ness Ziona, Israel Kim et al., 2000)) were pre-incubated with WT IL-18 or its mutated forms (30 ng/ml final concentration) and then added to cell cultures.

Figure 4A:
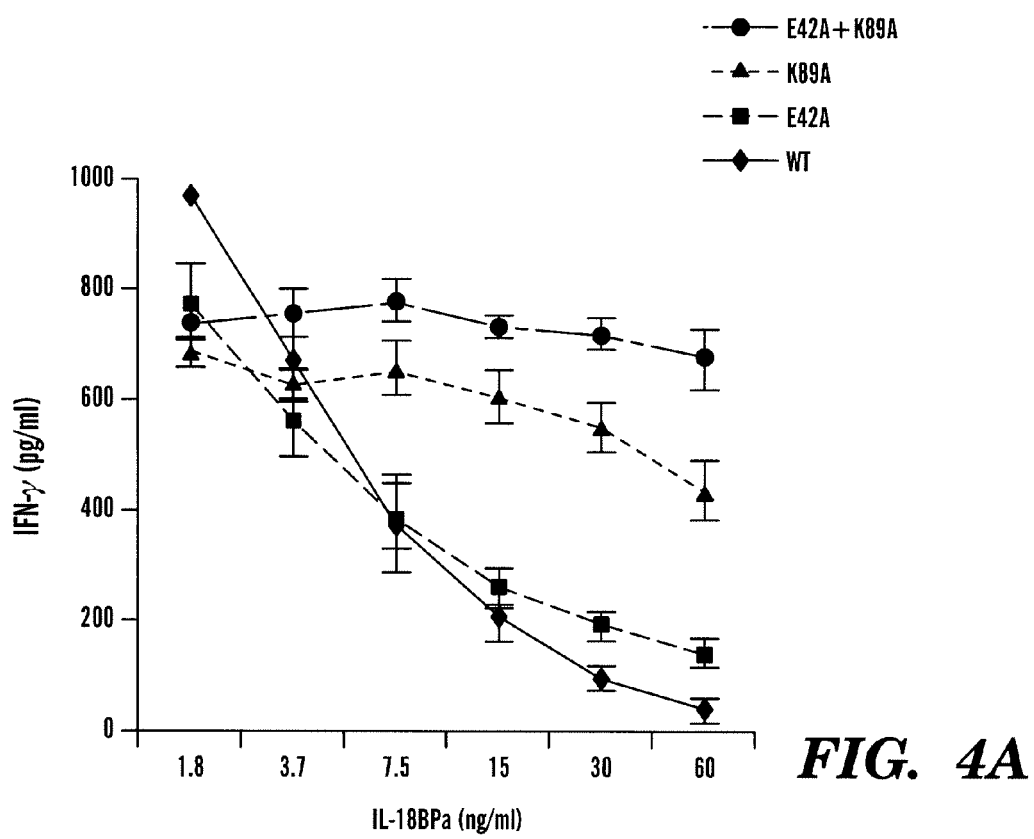
FIG. 4A shows the effect of IL-18BP in IFN-γ induction by human IL-18 WT and mutant protein in NKO cells. Mutants and WT IL-18 (30 ng/ml) were preincubated with IL-18BP at the concentrations indicated under the x axis (of FIG. 3B) for 1 h at room temperature and added to NKO cells stimulated with IL-12 (0.5 mg/ml).

As shown in FIG. 4A, the 50% inhibitory concentration of IL-18BP for co-induction of IFN-γ by WT IL-18 from NKO cells was approximately 15 ng/ml (assuming that no inhibition occurs at 3.7 ng/ml IL-18BP and this value represent 100% activity). The single mutation of E42A resulted in a similar dose-inhibitory concentration by IL-18BP.

Figure 5:
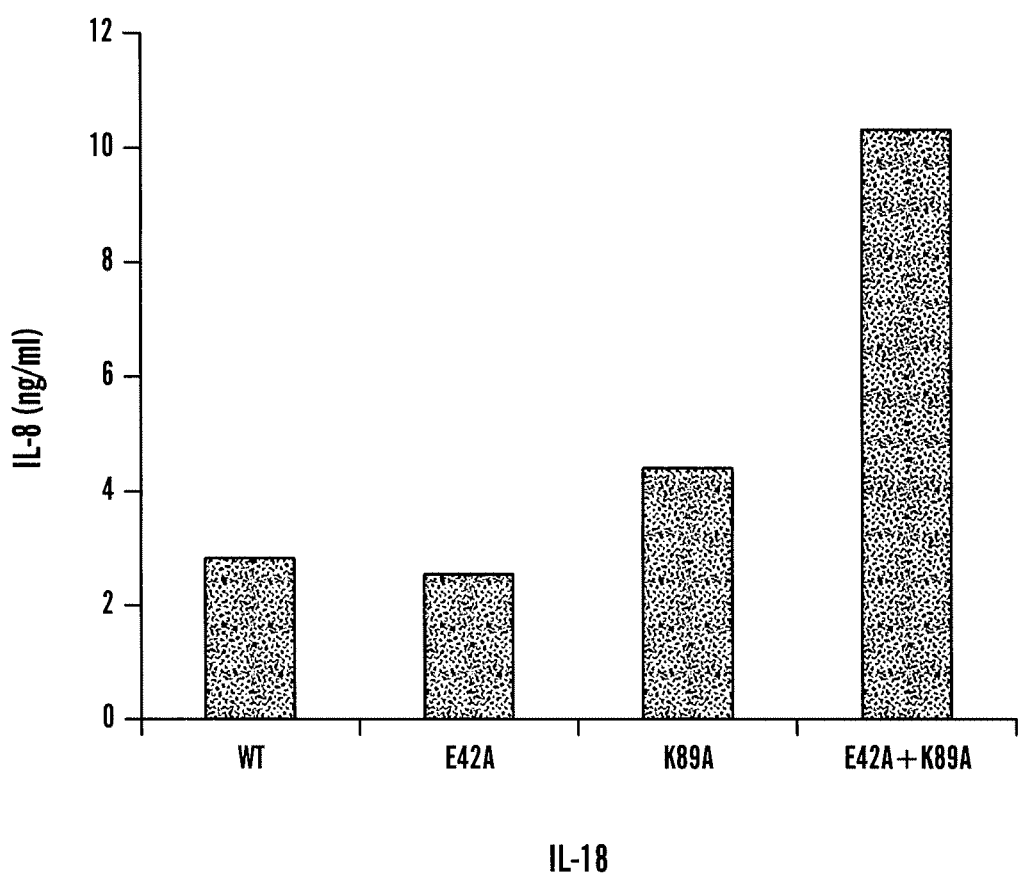
FIG. 5 shows the induction of IL-8 by IL-18 WT and mutant protein. PBMCs were incubated with IL-18 WT or mutant (30 ng/ml). Polymyxin B (1 µg/ml) was mixed with IL-18 for 30 min before being added to the PBMCs. After with primers Pr 1 and Pr 4 to generate a complete human IL-18 cDNA in which the ICE site is replaced by the factor Xa site (ICE/Xa).

However, when the mutant K89A was incubated with IL-18BP, its ability to act as a co-inducer of IFN-γ in NKO cells was neutralized at a lesser extent (FIG. 5A). Only at a concentration of 120 ng/ml a statistically significant reduction in activity could be observed. In contrast, IL-18BP failed to neutralize the double IL-18 mutant E42A/K89A.

Figure 4B:
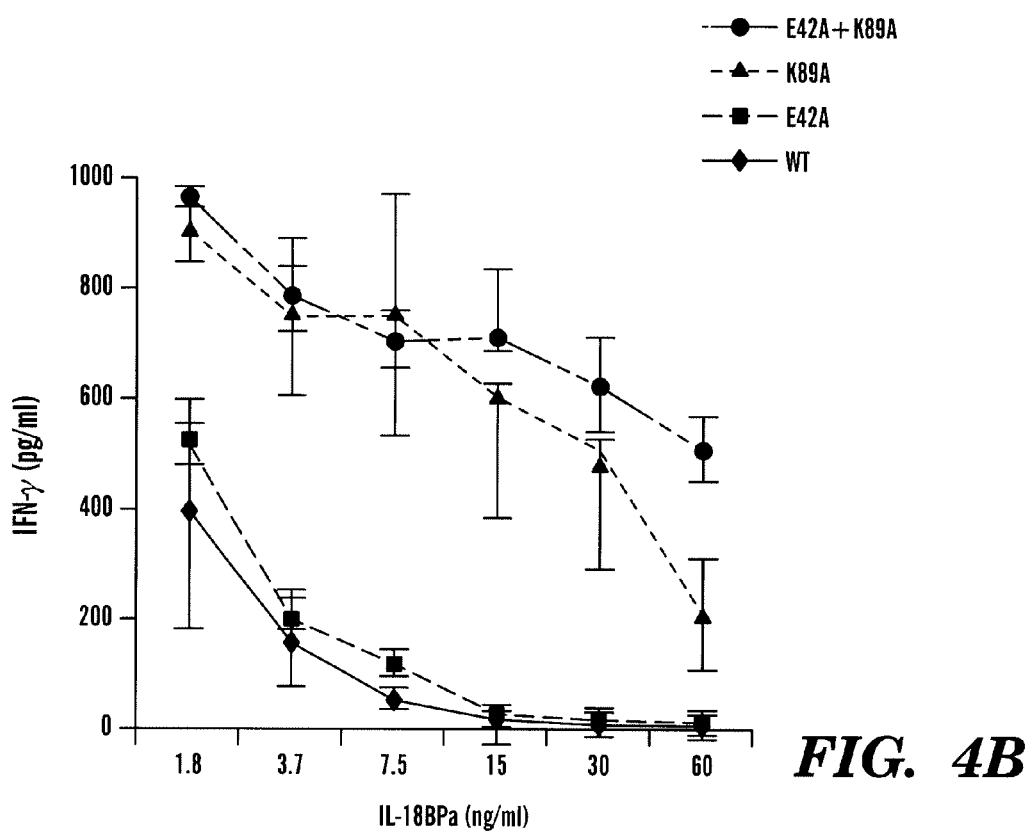
FIG. 4B shows the effect of IL-18BP in IFN-γ induction by human IL-18 WT and mutant protein in PBMCs cells. Mutants and WT IL-18 (30 ng/ml) were preincubated with IL-18BP at the concentrations, indicated under the x axis for 1 h at room temperature and added to PBMCs cells stimulated with IL-12 (1.0 mg/ml).

As shown in FIG. 4B IL-18 is more sensitive to neutralization by IL-18BP when tested in PBMCs rather than NKO cells. The amount of IL-18BP needed to neutralize WT IL-18 was 3.7 ng/ml, the lowest concentration tested. The single mutation E42A behaved similarly as WT IL-18, as established by the observation that low concentrations of IL18BP neutralized its biological activity in PBMCs. In contrast, the single mutation K89A was neutralized at 120 ng/ml. Similar to the results concerning neutralization of IL-18 mutants by IL-18BP in NKO cell, the double mutant E42A/K89A was only slightly affected by IL18-BP in PBMCs.

These results show that the mutant E89A and the double mutant E42A/K89A are less affected by the natural inhibitor IL-18BP.

Example 7

Isolation and Culture of Peripheral Blood Mononuclear Cells (PBMCs) and Induction of IFN-γ

Residual leukocytes from platelet plateletpheresis of healthy human donors were rinsed from blood tubing and subjected to centrifugation employing a conventional cell separation medium, e.g., over HISTOPAQUE® 1077 (polysuccrose, 5.7 g/dl, and sodium diatrizoate, 9 g/dl) sold by Signa Chemical Company, St. Louis, Mo. PBMCs were aspirated from the interface, washed three times in pyrogen-free saline (Baxter Health Care, Mundelein, Ill.), and resuspended at $5\times10^6$ cells per ml in RPMI 1640 medium supplemented with 10% FBS (GIBCO/BRL Grand Island, N.Y.). The cells were cultured in flat-bottomed 96-well plates (Becton Dickinson) with RPMI 1640 medium only (control), varying concentrations of recombinant human IL-18, and WT IL-18 (ICF/Xa) or the three mutants, in the presence of 1 ng/ml IL-12. In some experiments, IL18 preparations were first mixed with polymyxin B (1 µg/ml purchased from Sigma) before being added to the cells. Cells were incubated for 16-20 h at 37° C. in humidified air with 5% $CO_2$, and the culture supernatant was then collected for IFN-γ measurement.

Example 8

Induction of IFN-γ in NKO Cell Line

The original parental NK92 cell line was obtained from Hans Klingerman (Gong et al., 1994). The human NKO cell line used in the present studies was a subclone of this cell line. NKO cells were maintained in supplemented RPMI 1640 medium containing 10% FBS and 50 pg/ml of IL-2 (R&D Systems) and 200 pg/ml of IL-15 (PeproTech). For assays, NKO sells were suspended at $0.5 \times 10^6$ cells per ml in RPMI 1640 medium and stimulated in 0.2 ml volumes in 96-well plates with 0.5 ng/ml of IL-12 (PreproTech Rocky Hill, N.J.) and different concentrations of recombinant human IL-18 WT, IL-18 (ICE/Xa), or E42A, K89A and E42A/K89A IL-18 mutants. After 16-20 h at 37° C. in humidified air with 5% $CO_2$, the culture supernatant was collected for IFN-γ measurement.

Example 9

Analysis of Cytokines

The liquid-phase electrochemiluminescence (ECL) method was used to measure IFN-γ (13) and IL-8 (12) in cell culture media. The amount of ECL was determined with the use of an Origen Analyzer (Igen, Gaithersburg, Md.). The limit of detection of IFN-γ and IL-8 was 62 pg/ml and 40 pg/ml, respectively.

Example 10

Statistical Analysis

Data are expressed as the mean±SEM. Group means were compared by ANOVA, with the use of Fisher's least significant difference. Statistical significance was accepted within 95% confidence limits. ANOVA and correlation analyses were performed with the statistical packages STATVIEW® 512+ (Brain Power, Calabasas, Calif.).

Example 11

Production of the Mature IL-18 Mutants in CHO Cells

For expression and secretion of mature IL-18 mutants in CHO cells, the DNA sequence encoding the mature protein of wild type and mutant IL-18BP is ligated to the sequence of the DNA sequence of the signal peptide of human growth hormone (hGH) by two PCR reactions similarly to the reactions described in example 1. The template for the first PCR reaction for the amplification of each IL-18 mutant is the corresponding construct from example 2 with sense primer (Pr 9) containing overlapping sequences of IL-18 and hGH signal peptide and reverse primers (Pr 10) encoding the last 12 nucleotides of the IL-18, a stop codon and a site for a restriction enzyme. For the amplification of the growth hormone signal peptide the plasmid pXGH is used as the template with a sense primer (Pr 11) containing a site for a restriction enzyme, the first 12 nucleotides of the hGH signal peptide and the reverse primer (Pr 12), containing overlapping sequences with the hGH signal peptide and IL-18 mature protein. The templates for the second PCR performed for the amplification of the fragment encoding the signal peptide of the hGH fused to the mature sequence of the IL-18, are the purified amplified fragments from the first PCR reaction and the primers Pr 10 and Pr 11 containing the restriction sites. The fusion fragment is purified, digested with the appropriate restriction enzymes and cloned into a mammalian expression vector.

The plasmids are used for transfecting CHO (DHFR-) cells together with a plasmid containing the mouse DHFR gene as a genetic marker. Resistant cells are isolated in a selective medium and assayed for IL-18 production by an ELISA assay.

The stably transfected cells are subjected to several cycles of gene amplification with increasing concentrations of MTX. At the end of the gene amplification process, clones are isolated by limiting dilution. After subcloning the clone that show high specific productivity and greater stability of production is selected for production.

REFERENCES

1. Anderson, D. M., Maraskovsky, E., Billingsley, W. L., Dougall, W. C., Tometsko, M. E., Roux, E. R., Teepe, M. C., DuBose, R. F, Cosman, D., Galibert, L. (1997) "A. homologue of the TNF receptor and its ligand enhance T-cell growth and dendritic-cell function." Nature, 390, 175-179.
2. Bazan, J. F., Timans, J. C. and Kaselein, R. A. (1996) "A newly defined interleukin-1?" Nature 379, 591.
3. Born, T. L, Morrison, L. A., Esteban, D. J., VandenBos, T., Thebeau, L. G., Chen, N., Spriggs, M. K., Sims, J. E., Buller, R. M. (2000) "A poxvirus protein that binds to and inactivates IL-18, and inhibits NK cell response." J Immunol 164, 3246-54.
4. Childs, R., Chernoff, A., Contentin, N., Bahceci, E., Schrump, D., Leitman, S., Read, E. J., Tisdale, J., Dunbar, C., Linehan, W. M., Young, N. S., Barrett, A. J. (2000) "Regression of metastatic renal-cell carcinoma after non-myeloablative allogeneic peripheral-blood stem-cell transplantation." N Engl J Med 343, 750-8.
5. Cho, D., Kim, T. G., Lee, W., Hwang, Y. I., Cho, H. I., Han, H., Kwon, O., Kim, D., Park, H., Houh, D. (2000) "Interleukin-18 and the costimulatory molecule B7-1 have a synergistic anti-tumor effect on murine melanoma; implication of combined immunotherapy for poorly immunogenic malignancy" J Invest Dermatol, 114, 928-34.
6. Coughlin, C. M., Salhany, K. E., Wysocka, M., Aruga, E., Kurzawa, H., Chang, A. E., Hunter, C. A., Fox, J. C., Trinchieri, G. and Lee, W. M. (1998) "Interleukin-12 and interleukin-18 synergistically induce murine tumor regression which involves inhibition of angiogenesis." J Clin Invest March, 101, 1441-52.
7. Engelmann, H., Aderka, D., Rubinstein, M., Rotman, D. and Wallach. D. (1989) "A tumor necrosis factor-binding protein purified to homogeneity from human urine protects cells from tumor necrosis factor toxicity" J. Biol. Chem. 264, 11974-11980.
8. Engelmann, H., Novick, D. and Wallach, D. (1990) "Two tumor necrosis factor-binding proteins purified from human urine. Evidence for immunological cross-reactivity with cell surface tumor necrosis factor receptors." J. Biol. Chem. 265, 1531-1536.
9. Ghayur, T., Banerjee, S., Hugunin, M., Butler, D., Herzog, L., Carter, A., Quintal, L., Sekut, L., Talanian, R., Paskind, M., Wong, W., Kamen, R., Tracey, D., and Allen, H. (1997) "Caspase-1 processes IFN-gamma-inducing factor and regulates LPS-induced IFN-gamma production." *Nature* 386, 619-623.
10. Gollob, J. A., Mier, J. W., Veenstra, K., McDermott, D. F., Clancy, D., Clancy, M., Atkins, M. B. (2000) "Phase I trial of twice-weekly intravenous interleukin 12 in patients with metastatic renal cell cancer or malignant melanoma: ability to maintain IFN-gamma induction is associated with clinical response." Clin Cancer Res, 5, 1678-92.
11. Gong, J. H., Maki, G., Klingemann, H. G. (1994) "Characterization of a human cell line (NK-92) with phenotypical and functional characteristics of activated natural killer cells." Leukemia 8:652.
12. Gu, Y., Kuida, K., Tsutsui, H., Ku, G., Hsiao, K., Fleming, M. A., Hayashi, N., Higashino, K., Okamura, H., Nakanishi, K., Kurimoto, M., Tanimoto, T., Flavell, R. A., Sato, V., Harding, M. W., Livingston, D. J., and Su, M. S. (1997) "Activation of interferon-gamma inducing factor mediated by interleukin-1beta converting enzyme." *Science* 275, 206-209
13. Kim, S. H., Eisenstein, M., Reznikov, L., Fantuzzi, G., Novick, D., Rubinstein, M. and Dinarello, C. A. (2000) "Structural requirements of six naturally occurring isoforms of the IL-18 binding protein to inhibit IL-18." *Proc Natl Acad Sci USA* 97, 1190-5.
14. Kohno, K., J. Kataoka, T. Ohtsuki, Y. Suemoto, I. Okamoto, M. Usui, M. Ikeda, and M. Kurimoto. (1997) "IFN-gamma-inducing factor (IGIF) is a costimulatory factor on the activation of Th1 but not Th2 cells and exerts its effect independently of IL-12." *J. Immunol.* 158:1541-1550.
15. Kugler, A., Stuhler, G., Walden, P., Zoller, G., Zobywalski, A., Brossart, P., Trefzer, U., Ullrich, S., Muller, C. A., Becker, V., Gross, A. J., Hemmerlein, B., Kanz, L., Muller, G. A., Ringert, R. H. (2000) "Regression of human metastatic renal cell carcinoma after vaccination with tumor cell-dendritic cell hybrids." *Nat Med*, 3, 332-6.
16. Nakamura, K., Okamura, H., Wada, M., Nagata, K. and Tamura, T. (1989). "Endotoxin-induced serum factor that stimulates gamma interferon production." Infect-Immun 57, 590-5 issn: 0019-9567.
17. Nakamura, K., Okamura, H., Nagata, K., Komatsu, T. and Tamura, T. (1993) "Purification of a factor which provides a costimulatory signal for gamma interferon production." *Infect. Immun.* 61, 64-70
18. Novick, D., Engelmann, H., Wallach, D. and Rubinstein. M. (1989) "Soluble cytokine receptors are present in normal human urine." *J. Exp. Med.* 170, 1409-14.
19. Novick, D., Cohen, B. and Rubinstein, M. (1992) "Soluble Interferon-alpha Receptor Molecules Are Present in Body Fluids." FEBS Lett 314, 445-8.
20. Novick, D., Cohen, B. and Rubinstein, M. (1994) "The Human Interferon alpha/beta Receptor—Characterization and Molecular Cloning." *Cell* 77, 391-400.
21. Novick, D., Kim, S., Fantuzzi, G., Reznikov, L. L., Dinarello, C. A. and Rubinstein, M. (1999) "Interleukin-18 Binding Protein: A Novel Modulator of the Th1Cytokine Response. *Immunity* 10, 127, 36.
22. Okamura, H., Tsutsui, H., Komatsu, T., Yutsudo, M., Hakura, A., Tanimoto, T., Torigoe, K., Okura, T., Nukada, Y., Hattori, K., Akita, K., Namba, M., Tanabe, F., Konishi, K., Fukuda, S., and Kurimoto, M. (1995) "Cloning of a new cytokine that induces IFN-gamma production by T cells." *Nature* 378, 88-91
23. Puren, A. J., Fantuzzi, G., Dinarello, C. A. (1999) "Gene expression, synthesis, and secretion of interleukin 18 and interleukin 1beta are differentially regulated in human blood mononuclear cells and mouse spleen cells." Proc Natl Acad Sci USA, 96, 2256-61.
24. Seki, S, Habu, Y., Kawamura, T., Takeda, K., Dobashi, H., Ohkawa, T., Hiraide, H. (2000) "The liver as a crucial organ in the first line of host defense: the roles of Kupffer cells, natural killer (NK) cells and NK1.1 Ag+T cells in T helper 1 immune responses." Immunol Rev 174, 35-46.
25. Simonet, W. S., Lacey, D. L., Dunstan, C. R., Kelley, M., Chang, M. S., Luthy, R., Nguyen, H. Q., Wooden, S., Bennett, L., Boone, T., Shimamoto, G., DeRose, M., Elliott, R., Colombero, A., Tan, H. L., Trail, G., Sullivan, J., Davy, E., Bucay, N., Renshaw-Gegg, L., Hughes, T. M., Hill, D., Pattison, W., Campbell, P., Boyle, W. J. (1997). "Osteoprotegerin: a novel secreted protein involved in the regulation of bone density." Cell, 89, 309-19.
26. Slavin, S. (2000) "Immunotherapy of cancer with alloreactive lymphocytes." N Engl J Med 343, 802-3.
27. Slavin, S., Or, R., Prighozina, T., Gurevitch, O., Aker, M., Panighari, S., Shapira, M., Nagle, A. (2000) "Immunotherapy of hematologic malignancies and metastatic solid tumors in experimental animals and man" Bone Marrow Transplant Suppl 2:S54-7.
28. Tsutsui, H., K. Nakanishi, K. Matsui, K. Higashino, H. Okamura, Y. Miyazawa, and K. Kaneda. (1996) "IFN-gamma-inducing factor up-regulates Fas ligand-mediated cytotoxic activity of murine natural killer cell clones". *J. Immunol.* 157, 3967-73 issn: 0022-1767.
29. Tuting, T., Wilson, C. C., Martin, D. M., Kasamon, Y. L., Rowles, J., Ma, D. I., Slingluff, C. L., Wagner, S. N., van der Bruggen, P., Baar, J., Lotze, M. T., Storkus, W. J. (1998) "Autologous human monocyte-derived dendritic cells genetically modified to express melanoma antigens elicit primary cytotoxic T cell responses in vitro: enhancement by cotransfection of genes encoding the Th1-biasing cytokines IL-12 and IFN-alpha." J Immunol. 160, 1139-47
30. Urushihara, N., Iwagaki, H., Yagi, T., Kohka, H., Kobashi, K., Morimoto, Y., Yoshino, T., Tanimoto, T., Kurimoto, M., Tanaka, N. (2000) "Elevation of serum interleukin-18 levels and activation of Kupffer cells in biliary atresia." J Pediatr Surg 35, 446-9.
31. Ushio, S., Namba, M., Okura, T., Hattori, K., Nukada, Y., Akita, K., Tanabe, F., Konishi, K., Micallef, M., Fujii, M., Torigoe, K., Tanimoto, T., Fukuda, S., Ikeda, M., Okamura, H., and Kurimoto, M. (1996) *J. Immunol.* 156, 4274-9
32. Vigers, G. P., Anderson, L. J., Caffes, P., Brandhuber, B. J. (1997) "Crystal structure of the type-I interleukin-1 receptor complexed with interleukin-1beta." *Nature* 386, 190-4.
33. Xiang, Y. and Moss, B. (1999) "IL-18 binding and inhibition of interferon gamma induction by human poxvirus-encoded proteins." Proc Natl Acad Sci USA 96, 11537-42.
34. Yasuda, H., Shima, N., Nakagawa, N., Mochizuki, S. I., Yano, K., Fujise, N., Sato, Y., Goto, M., Yamaguchi, K., Kuriyama, M., Kanno, T., Murakami, A., Tsuda, E., Morinaga, T., Higashio, K. (1998) "Identity of osteoclastogenesis inhibitory factor (OCIF) and osteoprotegerin (OPG): a mechanism by which OPG/OCIF inhibits osteoclastogenesis in vitro." Endocrinology, 139, 1329-37.

All references described herein are incorporated herein by reference.

We claim:

1. An isolated DNA encoding an interleukin-18 (IL-18) polypeptide comprising the amino acid sequence of SEQ ID NO: 2, except that one or more amino acid residues selected from the group consisting of Glu-42, Ile-85, Met-87, Lys-89, Met-96, Asp-130, Lys-132, Pro-143, Met-149, and Leu-189 are mutated.

2. The isolated DNA according to claim 1, wherein the polypeptide comprises the amino acid sequence of SEQ ID NO:3.

3. The isolated DNA according to claim 1, wherein the polypeptide comprises the amino acid sequence of encoding the polypeptide of SEQ ID NO:4.

4. The isolated DNA according to claim 1, wherein the polypeptide comprises the amino acid sequence of encoding the polypeptide of SEQ ID NO:5.

5. The isolated DNA according to claim 1, wherein the polypeptide comprises the amino acid sequence of encoding the polypeptide of SEQ ID NO:6.

6. The isolated DNA according to claim 1, wherein the polypeptide comprises the amino acid sequence of encoding the polypeptide of SEQ ID NO:7.

7. The isolated DNA according to claim 1, wherein the polypeptide comprises the amino acid sequence of encoding the polypeptide of SEQ ID NO:8.

8. The isolated DNA according to claim 1 further comprising a nucleic acid molecule a signal peptide.

9. The isolated DNA according to claim 8, wherein the signal peptide is that of a growth hormone.

10. A vector comprising the isolated DNA according to claim 1, wherein said vector is capable of expressing the polypeptide encoded by said isolated nucleic acid in an appropriate host cell.

11. The vector according to claim 10, wherein the host cell is prokaryotic.

12. The vector according to claim 11, wherein the DNA encodes a polypeptide selected from a group consisting of SEQ ID NO:3, SEQ ID NO:4 and SEQ ID NO:5.

13. The vector according to claim 10, wherein the host cell is a eukaryotic cell.

14. The vector according to claim 13, wherein the DNA encodes a polypeptide selected from a group consisting of SEQ ID NO: 6, SEQ ID NO: 7 and SEQ ID NO: 8.

15. The vector according to claim 13, comprising an isolated DNA according to claim 8.

16. The vector according to claim 13, comprising an isolated DNA according to claim 9.

17. The vector according to claim 14, wherein said DNA is ligated to DNA encoding the human growth hormone signal peptide.

18. A pharmaceutical composition comprising an isolated DNA molecule according to claim 1 and a pharmaceutically acceptable carrier.

* * * * *

SEQUENCE LISTING

<160> NUMBER OF SEQ ID NOS: 18

<210> SEQ ID NO 1
<211> LENGTH: 582
<212> TYPE: DNA
<213> ORGANISM: Homo sapiens

<400> SEQUENCE: 1

```
atggctgctg aaccagtaga agacaattgc atcaactttg tggcaatgaa atttattgac      60
aatacgcttt actttatagc tgaagatgat gaaaacctgg aatcagatta ctttggcaag     120
cttgaatcta aattatcagt cataagaaat ttgaatgacc aagttctctt cattgaccaa     180
ggaaatcggc ctctatttga agatatgact gattctgact gtagagataa tgcaccccgg     240
accatattta ttataagtat gtataaagat agccagccta gaggtatggc tgtaactatc     300
tctgtgaagt gtgagaaaat ttcaactctc tcctgtgaga acaaaattat ttcctttaag     360
gaaatgaatc ctcctgataa catcaaggat acaaaaagtg acatcatatt ctttcagaga     420
agtgtcccag acatgataa taagatgcaa tttgaatctt catcatacga aggatacttt      480
ctagcttgtg aaaagagag agaccttttt aaactcattt tgaaaaaga ggatgaattg       540 ggggatagat ctataatgtt cactgttcaa aacgaagact ag                        582
```

<210> SEQ ID NO 2
<211> LENGTH: 157
<212> TYPE: PRT
<213> ORGANISM: Homo sapiens

<400> SEQUENCE: 2

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
                20                  25                  30

Met Thr Asp Ser Asp Cys Arg Asp Asn Ala Pro Arg Thr Ile Phe Ile
            35                  40                  45

Ile Ser Met Tyr Lys Asp Ser Gln Pro Arg Gly Met Ala Val Thr Ile
        50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Gly Asp Glu Leu
    130                 135                 140

Gly Asp Arg Ser Ile Met Phe Thr Val Gln Asn Glu Asp
145                 150                 155
```

<210> SEQ ID NO 3
<211> LENGTH: 193
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
            20                  25                  30

Ile Glu Gly Arg Tyr Phe Gly Lys Leu Ala Ser Lys Leu Ser Val Ile
        35                  40                  45

Arg Asn Leu Asn Asp Gln Val Leu Phe Ile Asp Gln Gly Asn Arg Pro
    50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
            100                 105                 110

Glu Asn Lys Ile Ile Ser Phe Lys Glu Met Asn Pro Pro Asp Asn Ile
        115                 120                 125

Lys Asp Thr Lys Ser Asp Ile Ile Phe Phe Gln Arg Ser Val Pro Gly
    130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp
```

<210> SEQ ID NO 4
<211> LENGTH: 193
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
            20                  25                  30

Ile Glu Gly Arg Tyr Phe Gly Lys Leu Glu Ser Lys Leu Ser Val Ile
        35                  40                  45

Arg Asn Leu Asn Asp Gln Val Leu Phe Ile Asp Gln Gly Asn Arg Pro
    50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Ala Asp Ser Gln Pro Arg Gly Met
                85                  90                  95

Ala Val Thr Ile Ser Val Lys Cys Glu Lys Ile Ser Thr Leu Ser Cys
            100                 105                 110

Glu Asn Lys Ile Ile Ser Phe Lys Glu Met Asn Pro Pro Asp Asn Ile
        115                 120                 125

Lys Asp Thr Lys Ser Asp Ile Ile Phe Phe Gln Arg Ser Val Pro Gly
    130                 135                 140

His Asp Asn Lys Met Gln Phe Glu Ser Ser Ser Tyr Glu Gly Tyr Phe
```

```
                     145                 150                 155                 160
Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp

<210> SEQ ID NO 5
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
            20                  25                  30

Ile Glu Gly Arg Tyr Phe Gly Lys Leu Ala Ser Lys Leu Ser Val Ile
        35                  40                  45

Arg Asn Leu Asn Asp Gln Val Leu Phe Ile Asp Gln Gly Asn Arg Pro
    50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Ala Asp Ser Gln Pro Arg Gly Met
                85                  90                  95

Ala Val Thr Ile Ser Val Lys Cys Glu Lys Ile Ser Thr Leu Ser Cys
            100                 105                 110

Glu Asn Lys Ile Ile Ser Phe Lys Glu Met Asn Pro Pro Asp Asn Ile
        115                 120                 125

Lys Asp Thr Lys Ser Asp Ile Ile Phe Phe Gln Arg Ser Val Pro Gly
    130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp

<210> SEQ ID NO 6
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Tyr Phe Gly Lys Leu Ala Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45
```

```
Ile Ser Met Tyr Lys Asp Ser Gln Pro Arg Gly Met Ala Val Thr Ile
 50                  55                  60

Ser Val Lys Cys Glu Lys Ile Ser Thr Leu Ser Cys Glu Asn Lys Ile
 65                  70                  75                  80

Ile Ser Phe Lys Glu Met Asn Pro Pro Asp Asn Ile Lys Asp Thr Lys
                 85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Cys Glu
             115                 120                 125

Lys Glu Arg Asp Leu Phe Lys Leu Ile Leu Lys Lys Glu Asp Glu Leu
         130                 135                 140

Gly Asp Arg Ser Ile Met Phe Thr Val Gln Asn Glu Asp
145                 150                 155
```

<210> SEQ ID NO 7
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Tyr Phe Gly Lys Leu Glu Ser Lys Leu Ser Val Ile Arg Asn Leu Asn
 1                   5                  10                  15

Asp Gln Val Leu Phe Ile Asp Gln Gly Asn Arg Pro Leu Phe Glu Asp
                 20                  25                  30

Met Thr Asp Ser Asp Cys Arg Asp Asn Ala Pro Arg Thr Ile Phe Ile
             35                  40                  45

Ile Ser Met Tyr Ala Asp Ser Gln Pro Arg Gly Met Ala Val Thr Ile
 50                  55                  60

Ser Val Lys Cys Glu Lys Ile Ser Thr Leu Ser Cys Glu Asn Lys Ile
 65                  70                  75                  80

Ile Ser Phe Lys Glu Met Asn Pro Pro Asp Asn Ile Lys Asp Thr Lys
                 85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Cys Glu
             115                 120                 125

Lys Glu Arg Asp Leu Phe Lys Leu Ile Leu Lys Lys Glu Asp Glu Leu
         130                 135                 140

Gly Asp Arg Ser Ile Met Phe Thr Val Gln Asn Glu Asp
145                 150                 155
```

<210> SEQ ID NO 8
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Tyr Phe Gly Lys Leu Ala Ser Lys Leu Ser Val Ile Arg Asn Leu Asn
 1                   5                  10                  15

Asp Gln Val Leu Phe Ile Asp Gln Gly Asn Arg Pro Leu Phe Glu Asp
                 20                  25                  30
```

-continued

```
Met Thr Asp Ser Asp Cys Arg Asp Asn Ala Pro Arg Thr Ile Phe Ile
            35                  40                  45

Ile Ser Met Tyr Ala Asp Ser Gln Pro Arg Gly Met Ala Val Thr Ile
        50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Cys Glu
            115                 120                 125

Lys Glu Arg Asp Leu Phe Lys Leu Ile Leu Lys Lys Glu Asp Glu Leu
        130                 135                 140

Gly Asp Arg Ser Ile Met Phe Thr Val Gln Asn Glu Asp
145                 150                 155
```

<210> SEQ ID NO 9
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
            20                  25                  30

Ile Glu Gly Arg Tyr Phe Gly Lys Leu Lys Ser Lys Leu Ser Val Ile
        35                  40                  45

Arg Asn Leu Asn Asp Gln Val Leu Phe Ile Asp Gln Gly Asn Arg Pro
    50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
                100                 105                 110

Glu Asn Lys Ile Ile Ser Phe Lys Glu Met Asn Pro Pro Asp Asn Ile
            115                 120                 125

Lys Asp Thr Lys Ser Asp Ile Ile Phe Phe Gln Arg Ser Val Pro Gly
        130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
                180                 185                 190

Asp
```

<210> SEQ ID NO 10
<211> LENGTH: 157
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 10

Tyr Phe Gly Lys Leu Lys Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
atatgaattc atggctgctg aaccagtag                                    29

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aaagtaacgt ccttcgatgt tttc                                         24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gaaaacatcg aaggacgtta cttt                                         24

<210> SEQ ID NO 14
<211> LENGTH: 31
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 14
atatggatcc tagtcttcgt tttgaacagt g                                 31

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
taatttagat gcaagcttgc c                                            21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggcaagcttg catctaaatt a                                            21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ctggctatct gcatacatac t                                            21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agtatgtatg cagatagcca g                                            21
```